United States Patent [19]
Gunderson

[11] Patent Number: 5,776,168
[45] Date of Patent: Jul. 7, 1998

[54] EGM RECORDING SYSTEM FOR IMPLANTABLE MEDICAL DEVICE

[75] Inventor: Bruce D. Gunderson, Plymouth, Minn.

[73] Assignee: Medtronic, Inc., Minneapolis, Minn.

[21] Appl. No.: 627,306

[22] Filed: Apr. 3, 1996

[51] Int. Cl.[6] ............................................ A61N 1/37
[52] U.S. Cl. ............................................ 607/27; 607/9
[58] Field of Search ............................ 607/5, 9, 27, 28

[56] References Cited

U.S. PATENT DOCUMENTS

| | | | |
|---|---|---|---|
| 4,223,678 | 9/1980 | Langer. | |
| 4,295,474 | 10/1981 | Fischell. | |
| 4,727,877 | 3/1988 | Kallok. | |
| 4,830,006 | 5/1989 | Haluska. | |
| 5,117,824 | 6/1992 | Keimel. | |
| 5,342,402 | 8/1994 | Olson et al. | 607/5 |
| 5,487,754 | 1/1996 | Snell et al. | 607/27 |
| 5,513,645 | 5/1996 | Jacobson et al. | 128/710 |
| 5,522,852 | 6/1996 | White et al. | 607/5 |

FOREIGN PATENT DOCUMENTS 9218198  10/1992  WIPO.

OTHER PUBLICATIONS

Olson et al., "Onset and Stability for Ventricular Tachyarrhythmia Detection in an Implantable Pacer–Cardioverter–Defibrillator" *Computers in Cardiology*, Oct. 7–10, 1986, IEEE Computer Society. Press. pp. 167–170.

Arzbaecher et al., "Automatic Tachycardia recognition:", PACE, vol. 7, May–Jun. 1984, Part II. pp. 541–547.

Mead et al., "Evaluation and Potential Applications of a New Method for Measuring Pacing System Lead Impedance", PACE, vol. 18, Apr. 1995, Part II, p. 817.

*Primary Examiner*—William E. Kamm
*Assistant Examiner*—George R. Evanisko
*Attorney, Agent, or Firm*—Reed A. Duthler; Harold R. Patton

[57] ABSTRACT

An EGM recording system in an implantable medical device of the type comprising an implantable pulse generator (IPG) and a lead system including one or more sensing leads each having a proximal end coupled to the IPG and a distal end with at least one pace/sense electrode in contact with a patient's heart. A short interval counter (SIC) is incremented by oversense events occurring within a short interval (SI), that is shorter than typical fibrillation event intervals, following a preceding paced or sensed event (except for certain ventricular event sequences). At the same time, the near-field and/or far-field EGM is detected, digitized and temporarily stored in a FIFO buffer as EGM data. When the first oversense event is detected within the SI, a time limited epoch of the corresponding EGM data is stored in a register in a rolling buffer. Subsequent EGM epochs with date/time stamps are stored in other registers of the rolling buffer at programmed counts of the SIC on a FIFO basis. Associated data, e.g., a date/time stamp of the recorded event and the oversense interval triggering storage, may also be recorded in similar buffers. The stored EGM epochs and associated data are later telemetered out to an external programmer for analysis. Lead integrity problems (including loose connections of the lead to the IPG) or electromagnetic interference (EMI) causing oversensing by the sense amplifiers can be diagnosed from the EGM epochs and associated stored data.

31 Claims, 5 Drawing Sheets

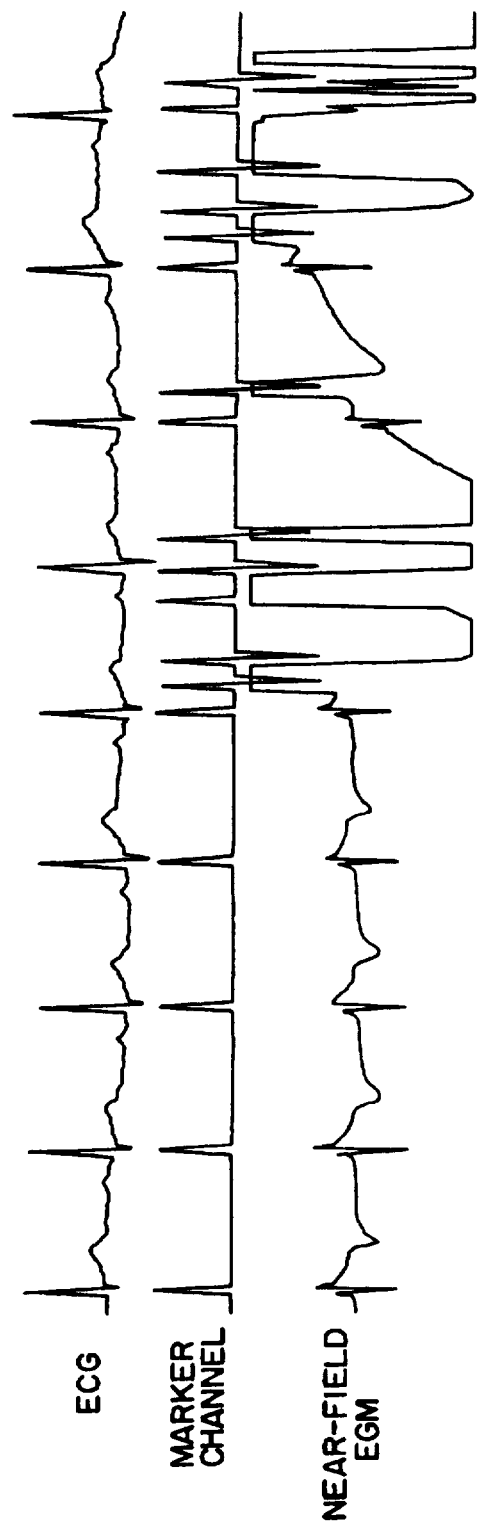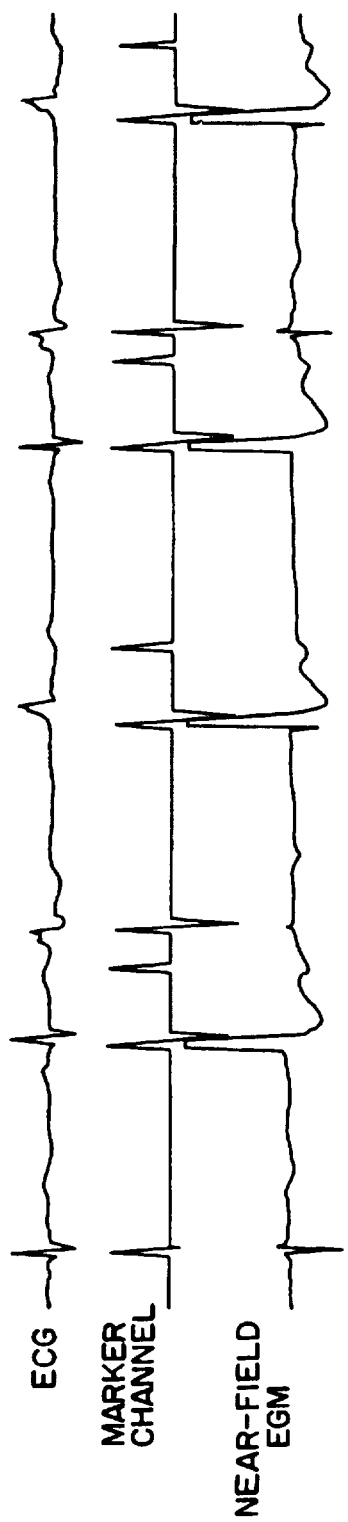
FIG.1 — START OF OVERSENSING
ECG / MARKER CHANNEL / NEAR-FIELD EGM
FIG.5 — POST PACE T-WAVE OVERSENSING
ECG / MARKER CHANNEL / NEAR-FIELD EGM

EGM RECORDING SYSTEM FOR IMPLANTABLE MEDICAL DEVICE

FIELD OF THE INVENTION

The present invention generally relates to implantable medical device and more particularly to a method and apparatus for recording EGM sequences in response to potential lead integrity failures in sensing leads associated with such devices.

BACKGROUND OF THE INVENTION

By way of definition, in the field of automatic implantable arrhythmia control devices, e.g. implantable cardioverter/defibrillators (ICDs) and implantable pacemaker/cardioverter/defibrillators (PCDs) the term "cardioversion" or "cardioverter" refers to the process of and device for discharging relatively high energy electrical shocks into or across cardiac tissue to arrest a life threatening tachyarrhythmia. The delivery of cardioversion shocks may or may not be synchronized with a cardiac depolarization or rhythm and may be applied to arrest a malignant ventricular tachycardia or ventricular fibrillation with a selectable or programmable shock energy. In practice, the arrest of atrial or ventricular tachycardia or fibrillation by such shocks delivered in synchrony with a cardiac depolarization is typically referred to as "cardioversion". Similarly, the arrest of atrial or ventricular fibrillation by a shock delivered without such synchronization is typically referred to as "defibrillation". In the following description and claims, it is to be assumed that these terms are interchangeable, and that use of one term is inclusive of the other device or operation, unless specific distinctions are drawn between them.

ICD systems have been implanted in patients over the preceding 15 years for detecting fibrillation or abnormal high rate tachycardia in a heart chamber and providing a fibrillation shock in the attempt to terminate the detected arrhythmia. Cardiac depolarizations of the particular heart chamber are sensed by sense amplifiers having inputs coupled to sense electrodes typically attached to the heart chamber as sensed events. The intervals between the sensed events are measured and compared to threshold fibrillation intervals. When detection criteria are satisfied, the defibrillation shock is delivered to the heart chamber.

Current arrhythmia control implantable pulse generators (IPGs) and associated lead systems for the treatment of tachyarrhythmias, e.g. the MEDTRONIC Model 7217 PCD IPG and associated leads, provide sensing of tachyarrhythmias and programmable staged therapies including anti-tachycardia pacing regimens and cardioversion energy and defibrillation energy shock regimens in order to terminate the sensed tachyarrhythmia with the most energy efficient and least traumatic therapies (if possible). The Model 7217 PCD IPG provides a programmable energy, single polarity wave form, shock from the discharge of a high voltage output capacitor bank through a pair of defibrillation electrodes disposed in relation to the heart. The Model 7217 PCD IPG also provides programmable single chamber bradycardia pacing therapies through the pace/sense electrodes.

In recent years, dual chamber cardiac pacemakers have also been proposed for incorporation into PCDs. The atrial and ventricular pacing pulse generators, sense amplifiers and associated timing operations are proposed to be incorporated into the system with atrial and ventricular pace/sense leads and electrodes. Various pacing modes may be programmed for recognizing and providing bradycardia and tachycardia pacing regimens.

Atrial or ventricular tachyarrhythmias are typically diagnosed in such systems by detecting a sustained series of short R-R or P-P intervals corresponding to an average high rate indicative of tachyarrhythmia or an unbroken series of short R-R or P-P intervals between R-waves or P-waves corresponding to such a high rate. The suddenness of onset of the detected high rates (short intervals), the stability of the high rates, or a number of other factors known to the art may also be measured at this time. Appropriate ventricular tachyarrhythmia detection methodologies measuring such factors are described in U.S. Pat. No. 4,830,006, incorporated herein by reference in its entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in *Computers in Cardiology*, Oct. 7–10, 1986, IEEE Computer Society Press, pages 167–170, also incorporated herein in its entirety. Other atrial tachycardia, fibrillation and flutter detection methodologies are disclosed in the article "Automatic Tachycardia Recognition", by Arzbaecher et al., published in *PACE*, Vol. 7, May–June 1984, part II, pages 541–547 and in PCT Application No. US92/02829, Publication No. WO 92/18198 by Adams et al., both incorporated herein by reference in their entireties. In the PCT application, careful synchronization of the high voltage atrial defibrillation pulse to the ventricles to avoid induction of ventricular tachycardia or fibrillation is also discussed.

In such PCD and ICD systems, and in pacing systems of all types, the integrity of the pace/sense leads and/or defibrillation leads, and the integrity of the connections of the proximal lead connector elements with IPG terminals, is of great importance. Lead insulation failures, interior lead conductor wire fracture or fractures with other lead parts, and loose, intermittent connections with the IPG connector terminals, e.g. loose set screws, can occur and are collectively referred to herein as lead integrity failures. Lead integrity failures can result in lead sensing failures as follows.

When pace/sense lead integrity is compromised, the lead impedance may increase or decrease, depending on the nature of the failure, affecting the sensing of cardiac signals (as well as the delivery of adequate energy to the heart during cardioversion/defibrillation and/or pacing therapies). If pace/sense lead integrity is not maintained, oversensing of artifacts generated in the lead and resembling high rate P-waves or R-waves can occur, resulting in a mis-diagnosis of a non-existent tachyarrhythmia. Or, undersensing due to the failure to conduct intrinsic high rate R-waves or P-waves to the sense amplifier can occur, resulting in a failure to diagnose an actual tachyarrhythmia. In the event that an atrial or ventricular tachyarrhythmia is mis-diagnosed, the applied anti-tachyarrhythmia pacing therapies or cardioversion/defibrillation shock therapies may themselves provoke a tachyarrhythmia episode. And, the tachyarrhythmia will not be treated in the event of a failure to recognize it. In the context of bradycardia pacing, inappropriate or insufficient pacing may be caused by undersensing or oversensing failures.

Consequently, a great deal of attention is paid to maintaining pace/sense lead integrity in the first place and to detecting pace/sense lead integrity failures before harm can occur to the patient. A pace/sense lead failure of the types described above may be a gradual process, and collected lead impedance data may signify an impedance change trend suggesting an impending failure that may be monitored more closely or may result in replacement of the lead or re-positioning of the lead electrode. An improvement in this process is described in the commonly assigned, co-pending U.S. patent application Ser. No. '08/346,661 filed Nov. 30, 1994 for AUTOMATIC LEAD RECOGNITION FOR AUTOMATIC IMPLANTABLE DEVICE and in an abstract by R. Mead M.D., et al., entitled "Evaluation and Potential Applications of a New Method for Measuring Pacing System Lead Impedance" PACE, April, 1995, Part II, p. 817. As shown therein, pace/sense lead integrity failures are detected by entering a test routine and directly injecting sub-threshold voltage pulses into a pair of the IPG connector terminals coupled to a pair of pace/sense lead connector elements (or into one such terminal/lead connector element and the IPG can electrode) and measuring current flow during delivery of the voltage pulse. The impedance of the circuit including the pace/sense lead pair impedance is determined as a simple function of the voltage divided by the current. A high variance from an impedance range specifications of the pace/sense lead(s) provide an indication of either a fracture in a pace/sense lead body or a connection failure of the lead connector end element with the IPG connector terminal. A low impedance variance from the lead impedance range specifications is indicative of an electrical short which may be present in a bipolar lead body due to a lead insulation failure. With respect to bipolar or multipolar leads, each lead conductor and associated electrode is tested in the same manner.

In cardiac pacemaker IPGs, the lead integrity check may also be undertaken during delivery of a pacing pulse. Pacing pulses are not perceptible, and therefore the patient is not aware that the testing is taking place, however, pacing may be inhibited because of oversensing due to a pace/sense lead integrity failure. (Consequently, it is preferred to conduct such testing at regular intervals independently from pacing as described in the above-referenced '661 application. The collected lead impedance data can be stored within IPG memory for transmission out to an external programmer through uplink telemetry on receipt of an interrogation command from the programmer.

This approach assumes that the lead integrity failures relatively gradually affect the pace/sense lead impedance. Moreover, it assumes that the failure mode affects lead impedance relatively constantly and the impedance change is not so transitory that it would be missed by the periodic testing. This may be the case with lead insulation failure modes, but may not be the case in other failure modes resulting in transient signals that may be detected and cause oversensing.

In the PCD and ICD system context, when undersensing or oversensing appears to be present, based on a patient's description of failure to provide a therapy when an arrhythmia is perceived or of therapies delivered in the absence of a perceived arrhythmia, respectively, impedance measurements may be undertaken. One difficulty with measuring lead impedance and using the results to gauge lead integrity lies again in the transitory nature of many lead failures or failures in the secure attachment of the lead connector element in the IPG connector block terminal. The condition may not be present when lead impedance is measured on a periodic basis.

With respect to oversensing, transient signals due to pace/sense lead integrity failures and to electromagnetic interference (EMI) have to be present in the pacing cycle when the sense amplifier is not blanked and when sense amplifier sensitivity is set to a suitable threshold level. Sense amplifier sensitivity is typically established in a patient work-up in the physician's facilities. Such sensitivity settings may be inappropriate when the patient is exposed to EMI sources at home, in the work place or elsewhere, leading to transitory oversensing episodes. When the patient reports the delivery of the therapy (which also may be stored in the IPG memory with a time stamp), it is difficult to ascertain the source of the problem. The testing of lead impedance may prove inconclusive. Physicians are averse to programming the therapies off to simply record the details of the sensed events and attempt to correlate them in time to a patient location and to then to physically locate the source of the problem.

When the impedance testing does not prove conclusive and there is no apparent sense amplifier sensitivity error or source of EMI, one other approach that has been undertaken is to provide the patient with an external monitor for recording the patient's far-field, external skin electrode, ECG in the hope of recording an oversensing or undersensing episode and establishing a diagnosis from it. In such PCD IPGs having "Marker Channel" capabilities for transmitting out sensed event markers and also having internal EGM recording and transmitting capabilities, the external monitor operates interactively with the PCD IPG to trigger transmission and recording of all three signals. The resulting recordings may be analyzed to determine the nature or suspected cause of oversensing and undersensing episodes.

Such an episode of oversensing is depicted in the strip from such a recording depicted in FIG. 1. The oversensing is evidenced by the additional sense marker pulses that are not synchronized with the ECG and EGM tracings of R-wave peaks. The additional sense event marker pulses evidence the sense amplifier response to other signals that are randomly generated and not associated with the patient's intrinsic ventricular heart depolarizations. The sources of such extra-ventricular sense events may lie in a lead integrity failure (as defined above) a sense amplifier sensitivity problem or a sense amplifier response to EMI. Given the rate at which these sense events are generated, their number, and the suddenness of onset, the PCD IPG may interpret the sequence as a high rate tachycardia or fibrillation and deliver an inappropriate shock therapy which at the least is extremely uncomfortable and frightening to the patient.

The external monitor is useful, but is practical only in the case where the patient has already experienced the frightening and painful delivery of a shock or the failure to respond to a tachyarrhythmia. In addition, the system disclosed in the above-referenced '661 application, while providing useful data, does not provide waveforms exhibiting the sense amplifier behavior.

Finally, it should be noted that many proposed and existing PCD IPGs have the capability of storing EGM data and sense detect data in relation to confirmed episodes of tachyarrhythmias that are treated by delivery of a therapy, as disclosed, for example U.S. Pat. Nos. 4,223,678 and 4,295, 474. The data storage also may include counts of confirmed tachyarrhythmias, therapies delivered and dates of detection and delivery. Depending on the available memory, one or more episodes, including 5 seconds or more of the EGM preceding and following the confirmation of the tachyarrhythmia and delivery of the therapy, may be digitized and stored in memory.

The storage of such data may, at times, be useful in detecting oversensing. However, it is only triggered on delivery of the therapy with the attendant patient alarm and discomfort. Moreover, the rate, onset and other criteria employed in the detection algorithms for detecting the tachyarrhythmia may not respond to oversensing. The high rate threshold for counting intervals as potential high rate tachycardia or fibrillation is typically on the order of 188–250 bpm, corresponding to high rate tachycardia and fibrillation intervals of about 240–320 ms. Once such a high rate tachycardia, fibrillation or flutter occurs, the intervals are too long for many exhibited oversensing episodes due to EMI or lead integrity failures.

In addition, even if sporadic episodes of oversensing due to EMI or lead integrity failures occur from time to time, initial episodes may not last long enough so that enough are counted in order to satisfy the detection criteria. Particularly, when lead integrity failures progress to the point that enough oversense events occur within the sensing intervals to satisfy a detection criteria, the lead may be in a failure mode that leads to continuous detection and delivery of a number of therapies which could prove dangerous to the patient. Many such PCD IPGs have a limit on the number, e.g. 4, of therapies that could be delivered in response to the continued detection of the arrhythmia following a preceding delivered therapy. However, the limit may in fact then make the PCD IPG non-responsive to a genuine tachyarrhythmia provoked by the delivery of the therapies.

In the example of FIG. 1, the some of the oversense events recur at intervals of about 130 ms. Some of the oversense events could be sensed within a fibrillation detection window. If the episode continued long enough, the detection criteria could be satisfied resulting in delivery of a therapy to the heart.

Accordingly, a need exists for a simple fully automatic and implantable system for detecting and recording such abnormal sense amplifier responses to transitory lead integrity failures or due to exposure to EMI. Such a system is needed from which the gradual deterioration of lead integrity can be determined well before the patient experiences a failure to deliver or inappropriate delivery of such a therapy.

SUMMARY OF THE INVENTION

It is therefore an object of the present invention to provide a practical and durable system incorporated into a PCD IPG for recording intervals of oversensing for later analysis that is not dependent on a delivered tachyarrhythmia therapy.

It is a further object of the present invention to provide such a system incorporated into a PCD IPG for recording intervals of oversensing for later analysis before the oversensing increases in frequency to the level that tachyarrhythmia detection criteria are satisfied by the oversense events.

These and other objects of the invention are realized in a method and apparatus implemented in a PCD IPG and operable in an EGM recording mode for recording an EGM epoch in an epoch window that precedes and follows the oversense episode upon satisfaction of short interval and accumulated oversense event criteria. In the practice of the present invention, a count of oversense events that fall within an oversense short interval (SI) accumulates over a prolonged period. When a programmable short interval counter (SIC) count is exceeded within the prolonged period, EGM data storage is triggered of the EGM (near-field or far-field) epoch associated with one or more oversense events. In a preferred embodiment, each time a multiple of the initial SIC count is exceeded, the storage of the EGM epoch related to the oversense event is stored. The count number and a date/time stamp may also be recorded with the particular EGM epoch.

Preferably the EGM epoch associated with the first oversense epoch to occur is stored and remains in storage until the stored data is read out in response to an interrogation command and telemetered out to the external programmer so that the beginning date/time may be ascertained. The more recent n EGM epochs and associated data may be stored on a FIFO basis in N stages of a rolling buffer.

The present invention may be implemented in dual chamber PCD systems for both the atrial and ventricular channels. In the ventricular chamber certain oversense events falling within the SI are excluded, namely a second oversense event detected following a ventricular pace. Such events typically result from a premature ventricular contraction (PVC) following a post-pace T-wave of an amplitude that is sensed as an oversense event. Such events are excluded because of their probable origin.

The stored near-field and/or far-field EGM epochs provide useful information to distinguish lead integrity failures from other possible causes of the frequently occurring oversense events, e.g., T-wave oversensing, R-wave double sensing, P-wave oversensing or the like. The physician may program the oversense recording algorithm including the number of short interval counter counts to trigger EGM epoch storage, the prolonged time period for accumulating the counts, and the short interval duration. From the resulting data, the physician may initiate a further external 24 hour monitor test or proceed directly to test and re-tighten a loose connection or replace the affected pace/sense lead, if necessary.

Patient environments may be tested for EMI by having the algorithm programmed on and all counters cleared shortly before entering the, suspect environment. If EMI is present and being sensed, the SIC count will increase rapidly, and the date/time of the first stored epoch can be related to the entry of the patient into the environment or a particular location of the patient in the environment. Moreover, if both near-field and far-field EGM epochs are stored, the comparison of the waveshapes may be of use in confirming EMI.

The present invention provides the physician with a tool for determining the likelihood of lead integrity or EMI affects well before they cause inappropriate delivery of therapies.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein:

FIG. 1 is an external monitor tracing illustrating oversensing of ventricular sensed events from a ventricular pace/sense lead;

FIG. 5 is a timing diagram illustrating the sequence of sensed events following a ventricular pace event that signifies a PVC.

DETAILED DESCRIPTION OF THE PREFERRED EMBODIMENTS

Figure 2:
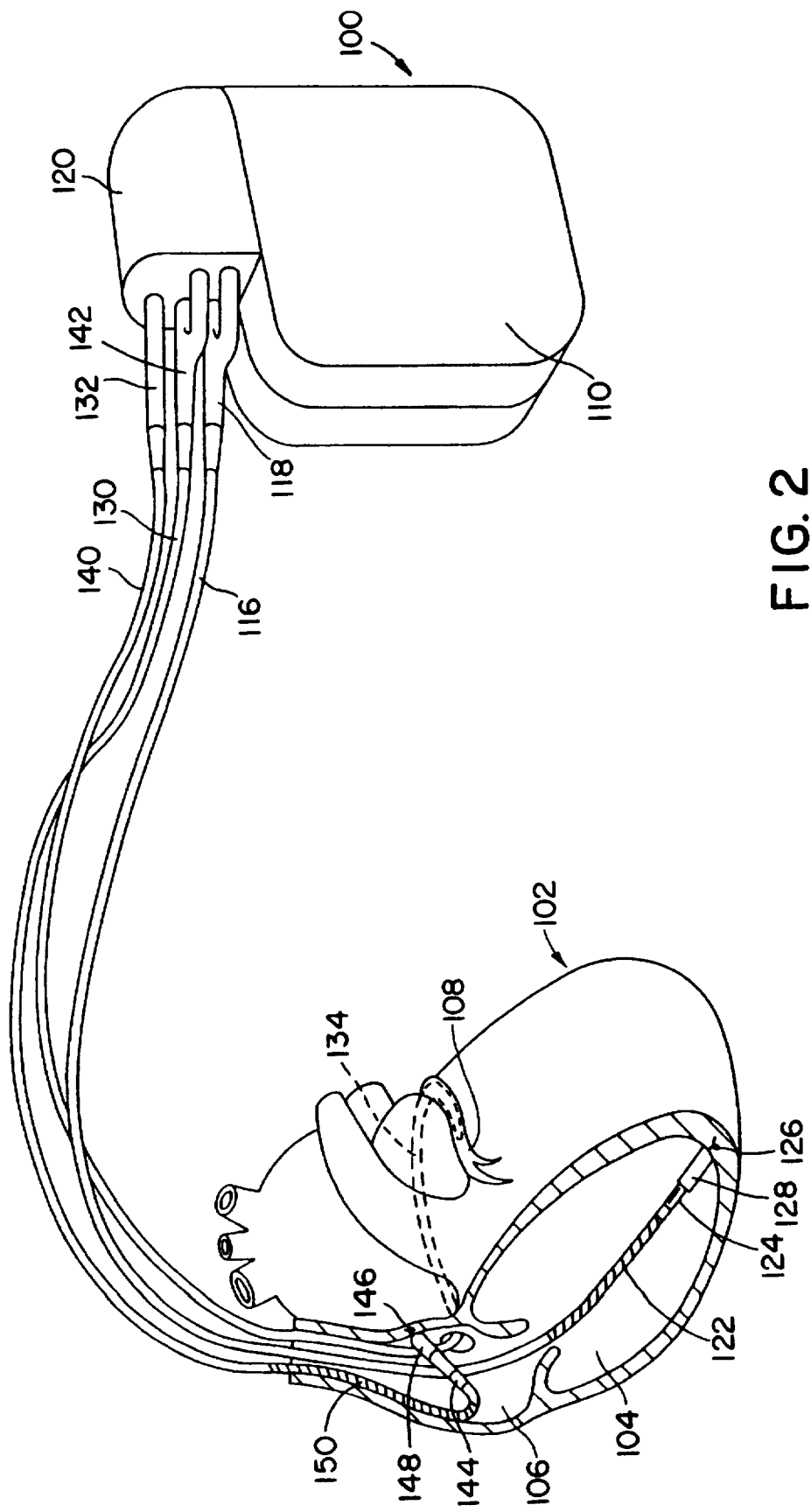
FIG. 2 is a schematic illustration of an exemplary atrial and ventricular chamber pacemaker/cardioverter/defibrillator IPG implanted in a patient's chest with am IPG can electrode and endocardial leads transvenously introduced into the RA, CS and RV of the heart wherein oversensing due to lead integrity failure or EMI may occur.

The preferred embodiments of the invention are preferably implemented in the context of an implantable PCD having single or dual chamber pacing and/or cardioversion/defibrillation capabilities of the types described in detail in commonly assigned, U.S. Pat. No. 5,312,441 and patent application Ser. No. 08/293,769 filed Aug. 19, 1994, for ATRIAL DEFIBRILLATOR AND METHOD OF USE, respectively, incorporated herein by reference in their entireties. Suoh PCDs may be constructed or made programmable to provide atrial only, ventricular only, or both atrial and ventricular pacing modes. The pacing modes also preferably include either or both bradycardia compensating pacing modes or anti-tachycardia pacing therapies. In addition, the present invention may be employed with a wide variety of cardioversion/defibrillation electrode combinations.

Returning to FIG. 1, it may be initially interpreted as the tracing from an external monitor to illustrate the data that is to be gathered by the IPG in accordance with the oversensing detection and EGM epoch data storage of the present invention. In this context, the upper tracing may be viewed as depicting a sequence of cardiac depolarization waveforms taken from a pair of far-field skin surface electrodes, and each event exhibits the classic PQRST waveform of intrinsic (non-paced), synchronized depolarization of the atria and ventricles. IPG generated Marker Channel pulses are depicted in the second tracing that track ventricular sense (VSENSE) events detected by a ventricular sense amplifier in the IPG. The VSENSE Marker Channel pulses are transmitted out to the external monitor and recorded by it in real-time sequence with the upper tracing. The lower tracing is a near-field EGM amplified by an IPG EGM sense amplifier coupled across the pair of ventricular pace/sense electrodes used in sensing of R-waves for detection of a bradyarrhythmia or tachyarrhythmia and from which the VSENSE Marker Channel pulses are generated. The third tracing is accomplished by recovery of the telemetered out EGM signal using a feature well known in the art.

In the initial sequence of depolarizations, the tracings exhibit normal sensing sinus rhythm behavior. However, oversensing commences with the fifth PQRST sequence as a result of a lead integrity failure as evidenced by a comparison of the second and third tracings to the first tracing. The first tracing continues to show normal intrinsic cardiac depolarizations, and consequently establishes that the oversensing is not due to external EMI or a fibrillation episode. The third tracing evidences intermittent saturation of the sense amplifier that typically occurs with intermittent signal artifacts generated by movement of a fracture in a pacing lead coupled to the sense amplifier. The second tracing follows the saturation transitions of the sense amplifier.

The scenario exhibited in FIG. 1 may also occur in the atrial sense channel. The oversense event episodes appear at times and then are absent for periods of time. As described above, typically such lead integrity failures progress and cause the oversense event episodes to occur for longer time periods, and certain of the oversense VSENSE events may fall into fibrillation or high rate tachycardia detection intervals and be counted toward the satisfaction of such tachyarrhythmia detection criteria. In accordance with the present invention, some of the oversense events that satisfy the SI criteria are counted and trigger storage of EGM epochs preceding and following the oversense events for telemetry out.

Figure 3:
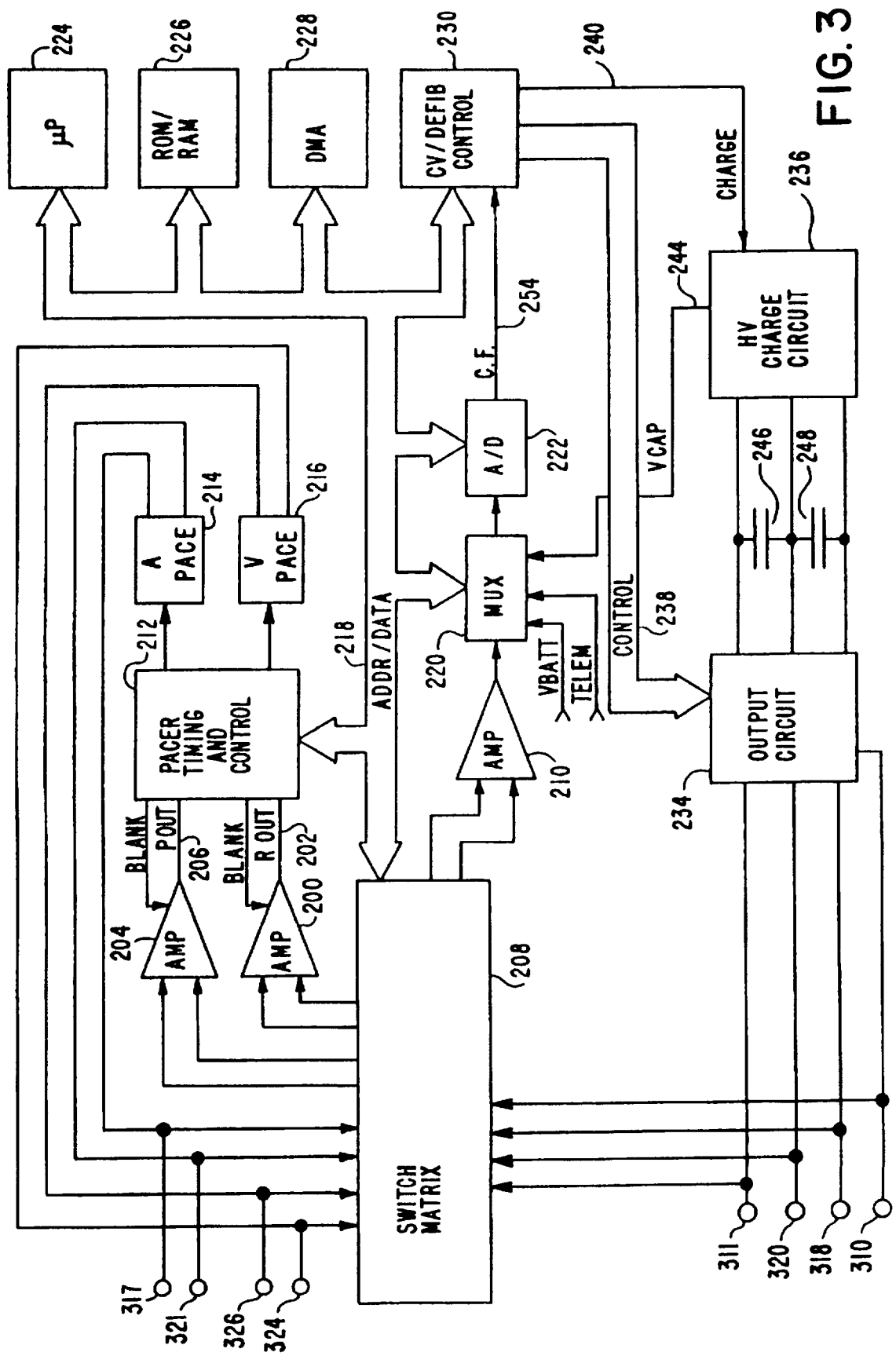
FIG. 3 is a block diagram of the PCD IPG of FIG. 2 in which the present invention may be practiced for storing near-field and/or far-field EGM epochs for both atrial and ventricular channels.

FIGS. 2 and 3 illustrate a dual chamber, multi-programmable, PCD IPG and associated lead system for providing atrial and/or ventricular sensing functions for detecting P-waves of atrial depolarizations and/or R-waves of ventricular depolarizations, depending on the programmed pacing and/or sensing mode and delivering pacing or cardioversion/defibrillation therapies in which the present invention may be practiced. An exemplary defibrillation lead system is depicted in FIG. 2 for delivering cardioversion/defibrillation shock therapies to the atria or ventricles of the heart. FIGS. 2 and 3 are intended to provide a comprehensive illustration of each of the atrial and/or ventricular, pacing and/or cardioversion/defibrillation configurations that may be effected using sub-combinations of the components depicted therein and equivalents thereto.

In the preferred embodiment of FIGS. 2 and 3, depending on the programmed pacing mode, pacing pulses may be applied to the atrium and/or ventricle in response to the detection of the appropriate bradycardia condition by the PCD IPG 100. The pacing and sensing functions are effected through atrial and ventricular bipolar pace/sense electrode pairs at the ends of right atrial/superior vena cava (RA/SVC) and right ventricular (RV) leads 140 and 116, respectively, fixed in the right atrium 106 and right ventricle 104, respectively, that are electrically coupled to the circuitry of IPG 100 through a connector block 120. Delivery of cardioversion or defibrillation shocks to the atrial and/or ventricular chambers of the heart 102 may be effected through selected combinations of the illustrated exemplar), RA and RV defibrillation electrodes on the RA/SVC and RV leads and an additional coronary sinus (CS) electrode on a CS lead 130 as well as an exposed surface electrode 110 of the outer housing or can of the IPG 100. The can electrode 110 optionally serves as a subcutaneous defibrillation electrode, used as one electrode optionally in combination with one intracardiac defibrillation electrode for cardioverting or defibrillating either the atria or ventricles. A remote, subcutaneous defibrillation patch electrode may be provided in addition to or substitution for the can electrode 110.

The RV lead 116 is depicted in a conventional configuration and includes an elongated insulating lead body, enclosing three concentric, electrically isolated, coiled wire conductors, separated from one another by tubular insulating sheaths. Located adjacent the distal end of the RV lead 116 are a pace/sense ring electrode 124, a helical, pace/sense electrode 126, mounted retractably within an insulating electrode head 128. Helical electrode 126 is adapted to be extended out of the electrode head 128 and screwed into the ventricular apex in a manner well known in the art. RV pace/sense electrodes 124 and 126 are each coupled to a coiled wire conductor within the RA lead body and are employed for cardiac pacing in the ventricle and for sensing near-field R-waves. RV lead 116 also supports an elongated, exposed wire coil, defibrillation electrode 122 in a distal segment thereof adapted to be placed in the right ventricle 104 of heart 102. The RV defibrillation electrode 122 may be fabricated from platinum, platinum alloy or other materials known to be usable in implantable defibrillation electrodes and may be about 5 cm in length. Defibrillation electrode 122 is also coupled to one of the coiled wire conductors within the lead body of RV lead 116. At the proximal end of the lead body is a bifurcated connector end 118 having three exposed electrical connectors, each coupled to one of the coiled conductors, that are attached within the connector block 120 to connector block terminals in a manner well known in the art.

The coronary sinus (CS) lead 130 includes an elongated insulating lead body enclosing one elongated coiled wire conductor coupled to an elongated exposed coil wire defibrillation electrode 134. CS defibrillation electrode 134, illustrated in broken outline, is located within the coronary sinus and great vein 108 of the heart 102 and may be about 5 cm in length. At the proximal end of the CS lead 130 is a connector end 132 having an exposed connector coupled to the coiled wire conductor and attached within the connector block 120 to connector block terminals in a manner well known in the art.

The RA/SVC lead 140 includes an elongated insulating lead body carrying three concentric, electrically isolated, coiled wire conductors separated from one another by tubular insulating sheaths, corresponding generally to the structure of the RV lead 116. The lead body is formed in a manner well known in the art in an atrial J-shape in order to position its distal end in the right atrial appendage. A pace/sense ring electrode 144 and an extendable helical, pace/sense electrode 146, mounted retractably within an insulating electrode head 148, are formed distally to the bend of the J-shape. Helical electrode 146 is adapted to be extended out of the electrode head 148 and screwed into the atrial appendage in a manner well known in the art. RA pace/sense electrodes 144 and 146 are employed for atrial pacing and for near-field sensing of P-waves. An elongated, exposed coil defibrillation RA/SVC electrode 150 is supported on RA lead 140 extending proximally to pace/sense ring electrode 144 and coupled to the third coiled wire conductor within the RA lead body. Electrode 150 preferably is 10 cm in length or greater and is configured to extend from within the SVC and toward the tricuspid valve. At the proximal end of the RA lead 140 is a bifurcated connector 142 which carries three exposed electrical connectors, each coupled to one of the coiled wire conductors, that are attached within the connector block 120 to connector block terminals in a manner well known in the art.

Preferably, bipolar pace/sense electrodes are employed in the practice of the invention, but their configuration, fixation in contact with, and positioning with respect to the atria and ventricles may differ from those shown in FIG. 2. Unipolar pace/sense electrode bearing leads may also be used in the practice of the invention, and the second, return electrode may be one or more of the defibrillation electrodes or the can electrode 110.

The PCD system configuration and operating modes of FIG. 2 may be varied by eliminating: (1) the atrial or ventricular pacing capability including the associated pace/sense electrodes thereby providing dual chamber cardioversion/defibrillation and single chamber bradycardia/tachycardia pacing capabilities; (2) in a single chamber PCD, the atrial or ventricular pacing and sensing capability along with the corresponding chamber cardioversion/defibrillation capability and associated leads and electrodes; (3) the atrial or ventricular cardioversion/defibrillation capability and associated lead and electrodes while retaining the dual chamber pacing and sensing capability thereby providing single chamber cardioversion/defibrillation and dual chamber bradycardia/tachycardia pacing capabilities; (4) in a special case of an atrial PCD, the ventricular cardioversion/defibrillation capability while retaining at least the atrial pace/sense capability and the ventricular sense capability for providing R-wave synchronization of the delivered atrial cardioversion therapies; or (5) the elimination of both atrial and ventricular pacing, wherein the system configuration may be referred to as an ICD system.

In accordance with the present invention, the detection of oversensing of the sense amplifier(s) and possible lead integrity failure of the associated lead or EMI effects on the sense amplifier(s) and lead(s) is automated so that the near-field and/or far-field EGM epochs may be stored for subsequent read-out. The circuitry within PCD IPG 100 communicates with an external programmer (not shown) through an RF communication link in a manner well known in the art. The storage of near-field and/or far-field EGM epochs and the associated short intervals, SIC counts, the programmed SI, the date/time stamp, and related parameters for each of the atrial and/or ventricular channels are effected via programmed-in commands. The stored EGM epochs are transmitted out on transmission of an interrogation command from the external programmer received by the PCD IPG circuitry. Such telemetry operations are well known in the art.

It should be noted that the lead integrity failures can include insulation failures between lead conductors or with the external environment of the body. Moreover, they may include loosening of the lead connector end connector elements from firm electrical and mechanical contact with connector elements within connector block 120 or fractures in other electrically conductive parts of the lead systems extending between the electrodes and the terminals within the connector block 120. It should also be noted that such lead integrity failures cause electrical artifacts that can occur with patient movement or exercise. It should also be noted that such lead integrity defects may also cause deterioration in the effectiveness of pacing therapies that may be delivered.

FIG. 3 is a functional schematic diagram of the circuitry of the dual chamber, implantable pacemaker/cardioverter/defibrillator 100 in which the present invention may usefully be practiced. Certain of the pace/sense and cardioversion/defibrillation functions may be disabled or not provided to configuire the PCD device to operate in other dual chamber or single chamber PCD or ICD system operating modes including the above-described modes (1)–(5). Therefore, FIG. 3 should be taken as exemplary of the circuitry of the type of PCD IPG 100 in which the invention may be embodied, and not as limiting, as it is believed that the invention may usefully be practiced in a wide variety of device implementations, as long as sensing of the P-wave or R-wave is required.

The PCD IPG circuitry of FIG. 3 includes a high voltage section for providing relatively high voltage cardioversion/defibrillation shocks when needed in response to detection of a tachyarrhythmia, a low voltage pace/sense section for sensing P-waves and/or R-waves and providing relatively low voltage bradycardia pacing and anti-tachycardia pacing therapies, both operated under the control of a microcomputer including a microprocessor 224, ROM/RAM 226 and DMA 228. Other functions, including uplink and downlink telemetry with an external programmer for interrogating or programming operating modes and parameters, are also provided in a manner well known in the art.

The block diagram of FIG. 3 depicts the atrial and ventricular pace/sense and defibrillation lead connector terminals of the connector block 120. Assuming the electrode configuration of FIG. 2, the correspondence to the illustrated leads and electrodes is as follows: Optional terminal 310 is hard wired to electrode 110, that is, the un-insulated portion of the housing of the PCD IPG 100, and technically may be directly connected and not be part of the connector block 120. Terminal 320 is adapted to be coupled through RV lead 116 to RV cardioversion/ defibrillation electrode 122. Terminal 311 is adapted to be coupled through RA lead 140 to RA/SVC electrode 150. Terminal 318 is adapted to be coupled through CS lead 130 to CS defibrillation electrode 134. However, it will be understood that fewer terminals may be provided than depicted, and/or that one or more differing defibrillation leads, e.g. epicardial patch electrode and subcutaneous patch electrode bearing leads may also be employed for one or more of the depicted defibrillation electrode bearing leads.

Terminals 310, 311, 318 and 320 are coupled to high voltage output circuit 234. High voltage output circuit 234 includes high voltage switches controlled by CV/DEFIB CONTROL logic 230 via control bus 238. The switches within circuit 234 control which electrodes are employed and which are coupled to the positive and negative terminals of the capacitor bank including capacitors 246 and 248 during delivery of the intermediate and high voltage cardioversion and defibrillation shocks.

Terminals 324 and 326 of the connector block are adapted to be coupled through RV lead 116 to RV pace/sense electrodes 124 and 126 for sensing and pacing in the ventricle. Terminals 317 and 321 are adapted to be coupled through RA/SVC lead 140 to RA pace/sense electrodes 144 and 146 for sensing and pacing in the atrium. Terminals 324 and 326 are coupled to the inputs of R-wave sense amplifier 200 through switches in switch network 208. R-wave sense amplifier 200 which preferably takes the form of an automatic gain controlled amplifier providing an adjustable sensing threshold as a function of the measured R-wave signal amplitude. A VSENSE signal is generated on R-OUT line 202 whenever the signal sensed between electrodes 124 and 126 exceeds the current ventricular sensing threshold. Terminals 317 and 321 are coupled to the P-wave sense amplifier 204 through switches in switch network 208. P-wave sense amplifier 204 preferably also takes the form of an automatic gain controlled amplifier providing an adjustable sensing threshold as a function of the measured P-wave amplitude. An atrial sense (ASENSE) signal is generated on P-OUT line 206 whenever the signal sensed between pace/sense electrodes coupled to terminals 317, 321 exceeds the current atrial sensing threshold. The A-PACE and V-PACE output circuits 214 and 216 are also coupled to terminals 317, 321 and 324, 326, respectively. The atrial and ventricular sense amplifiers 204 and 200 are isolated from the A-PACE and V-PACE output circuits 214 and 216 by appropriate isolation switches within switch matrix 208 and also by blanking circuitry operated by A-BLANK and V-BLANK signals during and for a short time following delivery of a pacing pulse in a manner well known in the art. The general operation of the R-wave and P-wave sense amplifiers 200 and 204 may correspond to that disclosed in U.S. Pat. No. 5,117,824, incorporated herein by reference in its entirety.

The PCD IPG circuitry of FIG. 3 provides atrial and/or ventricular cardiac pacing for bradycardia and tachycardia conditions and synchronized cardioversion and defibrillation shock therapies for tachyarrhythmias in accordance with therapy regimes programmed by the physician. With respect to the pacing operations, the pacer timing and control circuitry 212 includes programmable digital counters which control the basic time intervals associated with bradycardia pacing modes including DDD, VVI, DVI, VDD, AAI, DDI and other modes of single and dual chamber pacing well known to the art. Pacer timing and control circuitry 212 also controls escape intervals associated with timing and delivering anti-tachyarrhythmia pacing in both the atrium and the ventricle, employing any anti-tachyarrhythmia pacing therapies known to the art. In the process, pacer timing and control circuitry 212 also times the operation of and processes ASENSE and VSENSE events on the P-OUT and R-OUT lines of the atrial and ventricular sense amplifiers 204 and 200. In the context of the present invention, pacer timing and control circuitry 212 responds to commands from microprocessor 224 to initiate a threshold determination operation and controls the switch matrix 208 to select the appropriate threshold sensing electrode pair, controls the use and operation of EGM amplifier 210 or the atrial and/or ventricular sense amplifiers 204, 200 in the threshold detection operation, and processes the sensed events all as described below.

In normal pacing modes of operation, intervals defined by pacer timing and control circuitry 212 include atrial and ventricular pacing escape intervals, blanking intervals, the refractory periods during which sensed P-waves and R-waves are ineffective to restart timing of the escape intervals, and the pulse widths of the pacing pulses. These intervals are determined by microprocessor 224, in response to stored data in RAM in ROM/RAM 226 and are communicated to the pacer timing and control circuitry 212 via address/data bus 218. Pacer timing and control circuitry 212 also determines the amplitude of the cardiac pacing pulses under control of microprocessor 224.

During pacing, the escape interval counters within pacer timing and control circuitry 212 are reset upon sensing of R-waves and P-waves as indicated by a signals on lines 202 and 206. In accordance with the selected pacing mode, pacer timing and control circuitry 212 provides pace trigger signals to the A-PACE and V-PACE output circuits 214 and 216 on timeout of the appropriate escape interval counters to trigger generation of atrial and/or ventricular pacing pulses. The pacing escape interval counters are also reset on generation of pacing pulses, and thereby control the basic timing of cardiac pacing functions.

With respect to anti-tachyarrhythmia pacing, the value of the counts present in the escape interval counters when reset by sensed R-waves and P-waves may be used as measures of the durations of R-R intervals, P-P intervals, P-R intervals and R-P intervals, which measurements are stored in RAM in ROM/RAM 226 and used to detect the presence of tachyarrhythmias as described below.

Microprocessor 224 operates as an interrupt driven device, and is responsive to interrupts from pacer timing and control circuitry 212 corresponding to the occurrence sensed P-waves (ASENSE) and R-waves (VSENSE) and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts.

For example, in response to a sensed or paced ventricular depolarization or R-wave, the intervals separating that R-wave from the immediately preceding R-wave, paced or sensed (R-R interval) and the interval separating the paced or sensed R-wave from the preceding atrial depolarization, paced or sensed (P-R interval) may be stored. Similarly, in response to the occurrence of a sensed or paced atrial depolarization (P-wave), the intervals separating the sensed P-wave from the immediately preceding paced of sensed atrial contraction (P-P Interval) and the interval separating the sensed P-wave from the immediately preceding sensed or paced ventricular depolarization (R-P internal) may be stored. Preferably, a portion of RAM in the ROM/RAM 226

(FIG. 3) is configured as a plurality of recirculating buffers, capable of holding a preceding series of measured intervals, which may be analyzed in response to the occurrence of a pace or sense interrupt to determine whether the patient's heart is presently exhibiting atrial or ventricular tachyarrhythmia.

Detection of atrial or ventricular tachyarrhythmias, as employed in the present invention, may correspond to tachyarrhythmia detection algorithms known to the art. For example, presence of atrial or ventricular tachyarrhythmia may be confirmed by means of detection of a sustained series of short R-R or P-P intervals of an average rate indicative of tachyarrhythmia or an unbroken series of short R-R or P-P intervals. The suddenness of onset of the detected high rates, the stability of the high rates, or a number of other factors known to the art may also be measured at this time. In the event that an atrial or ventricular tachyarrhythmia is detected, and in antitachyarrhythmia pacing regimen is prescribed, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246 and 248 via charging circuit 236, under control of high voltage charging control line 240. The voltage on the high voltage capacitors is monitored via VCAP line 244 and applied to multiplexer 220, A/D converted in A/D converter/comparator 222 and compared to a predetermined value set by microprocessor 224 resulting in generation of a logic signal on Cap Full (OF) line 254, terminating charging. Thereafter, timing of the delivery of the defibrillation or cardioversion pulse is controlled by pacer timing/control circuitry 212. Following delivery of the fibrillation or tachycardia therapy, the microprocessor 224 then returns the operating mode to cardiac pacing and awaits the next successive interrupt due to pacing or the occurrence of a sensed atrial or ventricular depolarization.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, the polarity of the electrodes and which electrodes are involved in delivery of the pulse. Output circuit 234 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in U.S. Pat. No. 4,727,877, incorporated by reference in its entirety.

In the event that, as in FIGS. 2 and 3, both atrial and ventricular defibrillation are available, ventricular defibrillation may be accomplished using higher pulse energy levels than required for atrial defibrillation and may employ the same or a different electrode set. For example, terminals 310, 311, 318 and 320 or only terminals 311, 318 and 320 may be employed for atrial defibrillation. Terminals 311, 320 and 310 might be employed for ventricular defibrillation, with terminal 311 (coupled to RA/SVC electrode 150) coupled to terminal 310 (can electrode 110). Alternatively, terminals 310, 318 and 320 may be employed, with terminal 318 (coupled to CS electrode 134) coupled to terminal 310. As a further alternative, terminals 311, 310, 318 and 320 might all be employed for ventricular defibrillation, with terminals 310, 311 and 320 coupled in common. As yet another alternative, only terminals 310 and 320 might be employed for ventricular defibrillation added or substituted for either of terminals 311 or 318 for treating ventricular fibrillation.

In modern implantable PCD IPGs, the particular therapies are programmed in during a patient work up by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On re-detection of tachycardia, a more aggressive anti-tachycardia pacing therapy may abe scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at antitachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that atrial or ventricular fibrillation is identified, the typical therapy will be delivery of a high amplitude defibrillation pulse, typically in excess of 10 joules in the case of ventricular fibrillation and about 1 joule or less in the case of atrial defibrillation. Lower energy levels will be employed for cardioversion. As in the case of currently available implantable pacemakers/ cardioverter/ defibrillators, and as discussed in the above-cited references, it is envisioned that the implitude of the defibrillation pulse may be incremented in response to failure of an initial pulse or pulses to terminate fibrillation.

The detection criteria for detection of a tachyarrhythmia and the particular selection of the defibrillation terminals and associated defibrillation electrodes for delivery of the physician prescribed therapies are not of primary importance in the practice of the present invention. The method of the present invention, however, is only practiced when the HV charge circuit 236 is not being operated in response to a detected tachyarrhythmia and when cardioversion/ defibrillation therapies are not being delivered.

In accordance with the present invention, when the oversensing detection operation is enabled for the atrial or ventricular channel, the timing of successive ASENSE or VSENSE events are compared to a short interval in pacer timing and control circuitry 212. The short interval is generally greater than the blanking interval of the sense amplifier 204 or 200, which may be 120 ms for example, and may be (but not necessarily) shorter than the shortest tachyarrhythmia detection interval, which may be about 120 ms for the atrium and 160 ms for the ventricle. A suitable short interval may be 140 ms from the preceding A-PACE or ASENSE or V_PACE or VSENSE. Each ASENSE of VSENSE falling outside the 120 ms blanking interval but falling within the 140 ms short interval is classified as an oversense event. The atrial and ventricular oversense events increment an SIC in pacer timing and control circuitry 212

(except for certain ventricular oversense events as described below with respect to FIG. 4).

In the oversense detection mode of the present invention, switch matrix 208 is also used in an EGM sensing and data recording mode to select which of the available pace/sense electrode pairs, or a pace/sense electrode and a further electrode, are coupled to the inputs of wide band (0.5–200 Hz) EGM sense amplifier 210 for use in digital signal storage of the patient's near-field or far-field atrial and ventricular EGM. Therefore, the terminals 317, 321, adapted to be coupled to the atrial pace/sense electrodes 144, 146, and the terminals 324, 326, adapted to be coupled to the ventricular pace/sense electrodes 124, 126, are also coupled to the switch matrix 208. Switches within switch matrix 208 are selectively controlled by the microprocessor 224 or circuits within the pacer timing and control circuitry 212, via data/address bus 218, to couple the terminals 317, 321 or 324, 326 to the inputs of EGM amplifier 210 and to thereby apply atrial or ventricular near-field signals to the EGM amplifier 210. Alternatively, the switches are set so that one of the atrial terminal 317 or 321 and the can electrode terminal 310 or one of the ventricular terminals 324 or 326 and the can electrode terminal 310 are coupled to the inputs of EGM amplifier 210 and to thereby apply atrial or ventricular far-field signals to the EGM amplifier 210. Of course, EGM amplifier 210 may be duplicated for the atrial and ventricular channels and for near-field and far-field signal sensing and amplification. In all such cases, the input terminals of the EGM amplifier 210 are protected from the delivery of A-PACE and V-PACE pulses, and the delivery of any cardioversion/defibrillation shocks, in the same manner as the input terminals of the atrial and ventricular sense amplifiers 204 and 200.

The use of the EGM amplifier 210 for this function allows the continued, simultaneous processing of the P-OUT and R-OUT signals of the atrial and ventricular sense amplifiers 204 and 200 by the pacer timing and control circuitry and microprocessor 224 to detect the onset of a tachyarrhythmia requiring interruption of the threshold test operation, opening of the switches in the switch matrix 208, and commencement of delivery of an appropriate therapy. Moreover, in accordance with the present invention, the detection of oversense events and incrementing of the SIC may continue as the selected EGM signal is processed.

The output signals from EGM amplifier 210 are provided to multiplexer 220, and thereafter converted to multi-bit digital signals by A/D converter 222 for storage in RAM in ROM/RAM 226 under control of DMA 228. In this regard, the digitized signals may be temporarily stored in a buffer holding 10 seconds of the digitized EGM on a FIFO basis (preferably, 5 seconds recorded before and after the sensed event). When an SIC is incremented to a predetermined, preferably programmed-in, count, the digitized EGM in the buffer and the associated buffer count and date/time stamp are transferred to a specific storage rolling buffer in RAM in ROMTRAM 228.

In a further variation, the PCD IPG of FIGS. 1 and 2 is provided with the capability of measuring intervals between sensed and paced events and a subsequent sensed event and storing the intervals in a buffer in RAM in ROM/RAM 226 under control of DMA 228. The intervals are typically timed from the ASENSE and/or VSENSE output signals of the atrial sense amplifier 204 and/or ventricular sense amplifier 200, respectively, in the pacer timing and control circuitry 212. In this variation, the timed intervals may be temporarily stored in a buffer holding a predetermined number of intervals on a FIFO basis. In the context of the present invention, the actual timed interval of an oversense event triggering storage of an EGM epoch may also be recorded with the date/time stamp and other related data.

Figure 4:
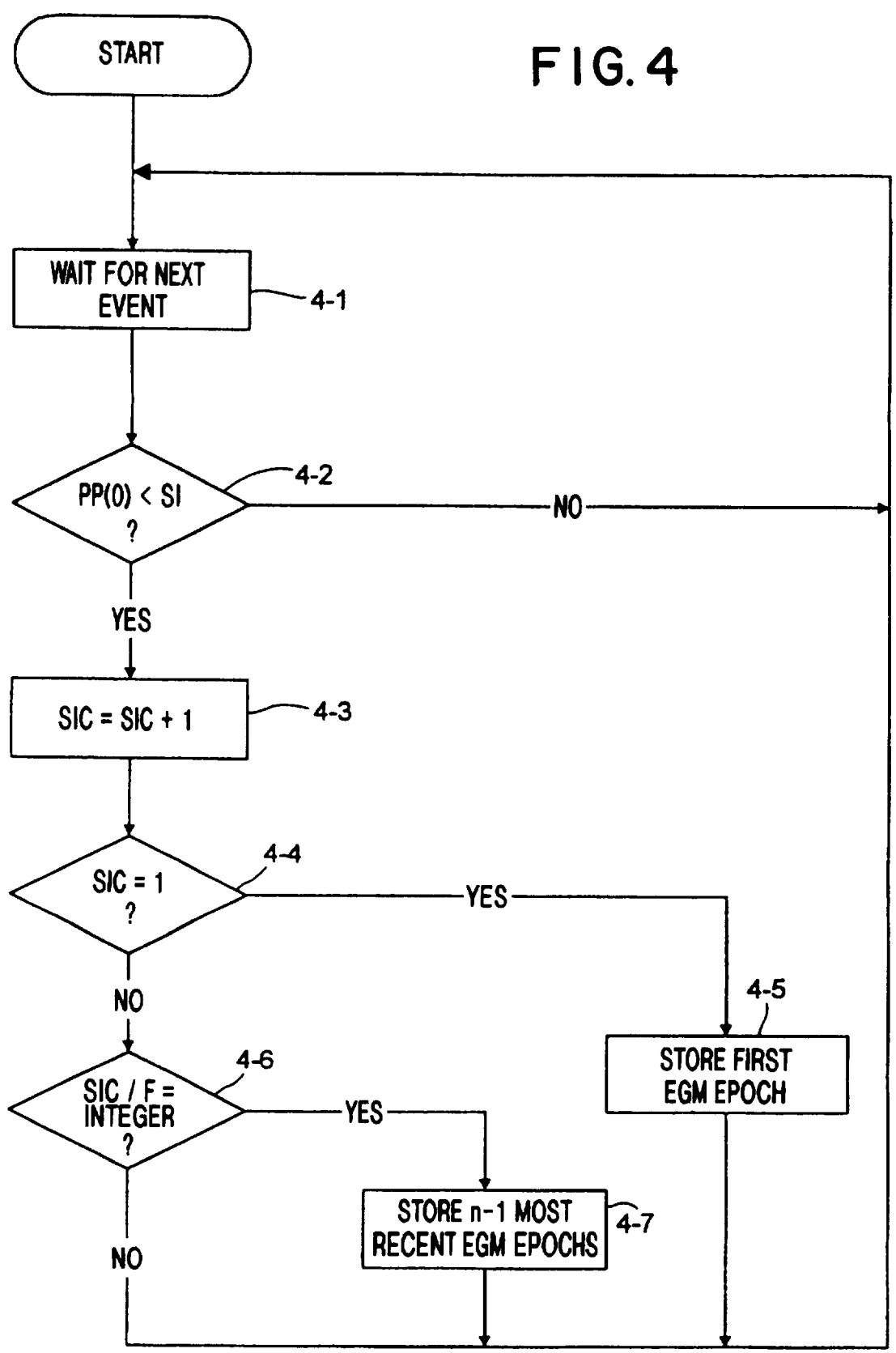
FIG. 4 is a flow chart of the EGM epoch recording algorithm of the present invention for the atrial channel.

The operation of the oversense detection mode in the atrial channel is depicted in FIG. 4 which depicts a processing method that may be implemented by pacer timing and control circuitry 212 on receipt of a programmed-in set of commands that is directed to and translated by microprocessor 224 into operating instructions. As stated earlier, the programmed-in commands may include the channel to be monitored, the near-field and/or far-field electrode selection, the duration of the oversense or short interval (SI), the counts of the SIC whereupon the digitized EGM is stored and optionally, the duration in hours that the algorithm will continue. The SIC may be software implemented but preferably is a counter in pacer timing and control circuitry 212.

In FIG. 4, the time between successive P-OUTs or between a preceding A-PACE and a P-OUT is referred to as the "PP" interval. At step 4-1, the next P-OUT sensed event is awaited, and when it occurs, the determination as to whether it is within the SI is made in step 4-2. If not, the process loops back to step 4-1. If it is within the SI, then the SIC is incremented in step 4-3. At step 4-4, the count of the SIC is compared to "1" in order to detect the initial ASENSE oversense event and to store its associate EGM epoch in an initial episode stage of the rolling buffer in step 4-5. If the SIC count exceeds "1", then the SIC count is processed in step 4-6 by dividing it by a frequency value "F" and comparing the result to an integer for example, the frequency value F may be programmed to 20. If the SIC count is between 2 and 19, the comparison is negative, and none of the EGM epochs associated with the detected ASENSE oversense event is stored. However, when the SIC count reaches 20 and integral multiples thereof, the EGM epoch that is simultaneously processed from the output signal of the EGM amplifier 210 is stored in the designated buffer of the RAM in step 4-7. The EGM epoch includes the current SIC count, the date/time stamp, and may include a designation of the far-field electrodes if it represents a far-field EGM. As noted above, the EGM epoch may also include both the near-field and the far-field EGM within the epoch window.

In the preferred embodiment, therefore, the first EGM epoch that is stored in the rolling buffer is retained, and the n-1 subsequent EGM epochs are stored on a FIFO basis in N-1 register stages in order to store the most recent EGM epochs. Other selections of EGM epochs to be saved may preferably be programmable.

It should be noted that the counted oversense events includes sensed events that fall within high rate tachycardia or fibrillation detection intervals and may he mistakenly counted toward satisfying the respective detection criteria. To the extent that it can be determined in a particular sequence in this context or in others that a sense event that falls within the SI is in fact due or reflects a cardiac contraction, then the above processes may be modified to exclude such sense events from being counted as an oversense events.

Figure 6:
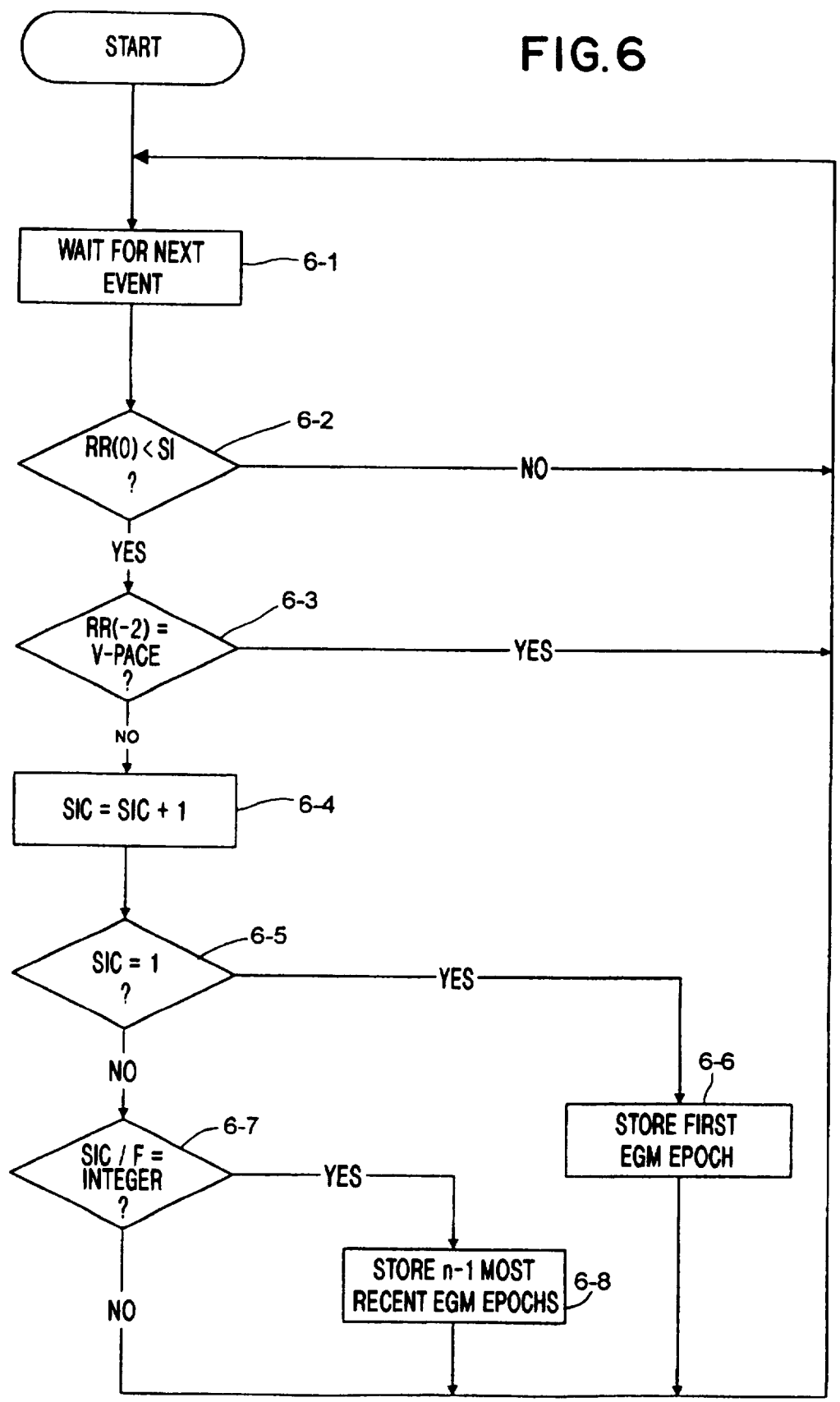
FIG. 6 is a flow chart of the EGM epoch recording algorithm of the present invention for the ventricular channel.

Such a modified process may be followed in regard to the ventricular oversensing mode of FIGS. 5 and 6. Turning to FIG. 5, it depicts a situation that may arise in the processing of the R-OUT signals that may occur following a V-PACE Again, the tracings from top to bottom are the far-field ECG the Marker Channel pulses and the near-field EGM. The V-PACE events are signified in the middle tracing by the biphasic pulses. In this patient, the ventricular sense amplifier detects the T-wave following each delivered V-PACE, but its detection is outside the SI. Occasionally, the V-PACE is followed by a sensed T-wave and then by a PVC that is within the SI interval started on the T-wave sense. As a result, the PVC would be counted as an oversense event. Because this scenario is fairly common, the algorithm of FIG. 6 is modified from that of FIG. 4 to exclude such events from being counted. Of course, this feature could be enabled or disabled by a programmable instruction entered by the physician for the particular patient.

Therefore, in FIG. 6, the process steps 6-1 and 6-2 correspond to steps 4-1 and 4-2 and steps 6-4 through 6-8 correspond to steps 4-3 through 4-7 as described above. Additional step 6-3 determines whether or not the oversense or SI R-OUT event was preceded by a paced event within the preceding two R-R time intervals.

The above methods (and associated EGM amplifier 210 and rolling buffer) may be duplicated for storing both near-field and far-field EGM data and for atrial and ventricular channel data accumulation at the same time. The episodes of oversensing of the type depicted in the tracings of FIG. 1 may be accumulated in the rolling buffer(s). At a later point in time, the oversense algorithm may terminate in accordance with its programmed-in time limit or may continue indefinitely until the physician has the opportunity to examine the patient and interrogate the SI EGM buffer contents. The present invention therefore allows considerable flexibility to the physician in programming the data accumulation, and the resulting data may be analyzed to determine if it demonstrates a lead integrity failure and/or merits further monitoring or intervention to replace the affected lead. Similarly, the data may be used to interpret the effects of EMI and identify its source.

The illustrated PCD IPG of FIG. 2 and block diagram of FIG. 3 are merely exemplary, and correspond to the general functional organization of most multi-programmable, microprocessor controlled, PCD devices presently commercially available. It is believed that the present invention is most readily practiced in the context of such an IPG architecture, and that the present invention can therefore readily be practiced using the basic hardware of existing microprocessor controlled, single chamber PCD IPGs, or in proposed dual chamber PCD devices of the types listed above. The invention may be implemented primarily by means of variations in the software stored in the ROM/RAM 226, switch matrix 208 and place timing and control circuitry 212 for the particular combinations of atrial and/or ventricular sense/pace and cardioversion/defibrillation functions in the particular PCD device configuration.

It should be noted that the present invention may also be employed to test for lead integrity failures in the defibrillation leads coupled to terminals 318, 311, 320 through the use of the EGM amplifier 210 and suitable digital processing of output signals exceeding a threshold value. The same signal processing may be undertaken in the event that oversense events occur on the tested defibrillation lead, suggesting a possible lead integrity failure.

While the preferred embodiment of the present invention has been described in the context of a PCD of FIG. 4, it will be understood that it may be practiced in the same manner as described above in single or dual chamber pacemakers. In this regard, the pacing and sensing circuitry of FIG. 4 may be viewed as single chamber or dual chamber pacing embodiments of the present invention.

The present invention may also be usefully practiced in all such configurations by means of a full custom integrated circuit in each case. For example, such a circuit may take the form of a state machine in which a state counter serve to control an arithmetic logic unit to perform calculations according to a prescribed sequence of counter controlled steps.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

I claim:

1. In an implantable cardiac medical device having the capability of sensing cardiac events on a sensing lead positioned in relation with the patient's heart and storing the electogram (EGM) of the heart in device memory in response thereto, a method of recording an EGM epoch in an oversensing condition comprising the steps of:

establishing oversense event criteria;

sensing cardiac events using the sensing lead;

establishing an oversense short interval following the sensing of a cardiac event;

identifying cardiac events sensed using said sensing lead occurring within said oversense short interval as oversense events;

counting oversense events to produce an oversense event count;

comparing the oversense event count with said oversense event criteria; and recording an EGM epoch using said sensing lead in said device memory in response to the oversense event count meeting said oversense event criteria.

2. The method of claim 1 wherein said recording step further comprises:

recording said EGM epoch over an EGM epoch time window that precedes and follows the oversense event in device memory in response to the oversense event count meeting said oversense event criteria.

3. The method of claim 2 wherein the recording step further comprises recording an EGM epoch each time that the oversense event count meets said oversense event criteria to produce a plurality of recorded EGM epochs.

4. The method of claim 3 wherein said recording step further comprises recording the EGM epoch in response to an oversense event count equal to one.

5. The method of claim 4 wherein said step of establishing the oversense event criteria comprises defining plurality of values and wherein said recording step farther comprises recording an EGM each time the oversense event count equals a said defined value.

6. The method of claim 1 wherein said step of recording an EGM epoch further comprises recording a far-field EGM epoch from said sensing lead.

7. The method of claim 1 wherein said step of recording an EGM epoch further comprises recording a near-field EGM epoch from said sensing lead.

8. The method of claim 1 further comprising the step of recording the date and time that the EGM epoch is recorded in device memory.

9. The method of claim 1 further comprising the steps of:

in conjunction with identifying sensed cardiac events as oversense events, measuring the interval separating an oversense event from a preceding paced or sensed event; and in conjunction with the recording step, recording the measured interval with the EGM epoch that is recorded in device memory in association with the oversense event.

10. In an implantable cardiac medical device having means for providing a cardiac therapy in response to a sensed condition and having device memory for storage of a cardiac electrogram (EGM), a system for responding to an oversense condition that may incorrectly result in provision of the therapy, comprising:

means for definiteness event count criteria;

a sensing lead having at least one sense electrode positioned in relation to a patient's heart;

sense amplifier means for sensing electrical signals conducted on the sensing lead including depolarizations of the heart and providing a sensed event signal in response thereto;

means for establishing an oversense short interval following a sensed event signal;

means for identifying sensed event signals occurring within said oversense short interval as oversense events;

means for counting the oversense events to produce an oversense event count;

means for comparing the oversense event count with oversense said event count criteria; and means for recording an EGM epoch from said lead system in said device memory in response to the oversense count meeting said oversense event count criteria.

11. The system of claim 10 wherein said recording means further comprises:

means for recording said EGM epoch over an EGM epoch time window that precedes and follows the oversense event in said device memory in response to said oversense count meeting said oversense event count criteria.

12. The system of claim 11 wherein said recording means comprises means for recording an EGM epoch each time that said oversense event count meets said oversense event count criteria.

13. The system of claim 12 wherein said recording means further comprises means for recording the EGM epoch in response to an oversense event count equal to one.

14. The system of claim 13 wherein said oversense event count criteria defining means comprises means for defining a plurality of values and said recording means further comprises means for recording EGM each time said oversense event count equals a said defined value.

15. The system of claim 10 wherein said recording means comprises means for recording an EGM epoch each time that said oversense event count meets said oversense event count criteria.

16. The system of claim 10 wherein:

said lead system comprises at least one sensing lead and first sensing electrode in proximal relation to said patient's heart and a further remote second sensing electrode; and said EGM epoch further comprises a far-field EGM epoch recorded from said first and second electrodes.

17. The system of claim 10 wherein:

said lead system comprises first and second sensing leads and electrodes in proximal relation to said patient's heart; and said EGM epoch further comprises a near-field EGM epoch recorded from said first and second electrodes.

18. The system of claim 10 further comprising:

means for recording the date and time that the EGM epoch is recorded in said device memory in association with the recorded EGM epoch.

19. The system of claim 10 further comprising:

means for timing the actual interval of an oversense event from a preceding paced or sensed event; and means for recording the timed actual interval with the EGM epoch that is recorded in said device memory in association with the oversense event.

20. In an implantable pulse generator having means for sensing cardiac events through a sensing lead coupled with a patient's heart, a device memory, means for recording an electrogram (EGM) in the device memory, means for determining the absence of a heart beat, and means for pacing the patient's heart in response thereto, a method of recording an EGM epoch in an oversensing condition for a determination of potential sensing lead integrity failure or electromagnetic interference comprising the steps of:

establishing oversense event criteria;

sensing cardiac events using the sensing lead;

establishing an oversense interval following a preceding sensed cardiac event sensed on said sensing lead in which a further cardiac sensed event may occur;

identifying sensed cardiac events occurring within said oversense interval as oversense events;

counting said oversense events to produce an oversense event count;

comparing the oversense event count with said oversense event criteria; and recording an EGM epoch in said device memory in response to said oversense event count meeting said oversense event criteria.

21. The method of claim 20 further comprising the step of recording a date and time that the EGM epoch is recorded in said device memory in conjunction with said recording step.

22. The method of claim 20 further comprising the steps of:

in conjunction with identifying sensed cardiac events as oversense events, measuring the interval separating an oversense event from a preceding paced or sensed event; and in conjunction with said recording step, recording the measured interval with the EGM epoch that is recorded in said device memory in association with the oversense event.

23. In an implantable pulse generator having means for sensing ventricular events through a sensing lead coupled with the ventricle of a patient's heart, a device memory means for recording a ventricular electrogram (EGM) in said device memory, and means for generating ventricular pace pulses for pacing the patient's heart, a method of recording an EGM epoch in an oversensing condition of ventricular sensed events for a determination of potential sensing lead integrity failure or electromagnetic interference comprising the steps of:

establishing oversense event criteria;

sensing ventricular events using the sensing lead;

establishing an oversense interval following a preceding ventricular sensed event or ventricular pace pulse in which a further ventricular sensed event may occur;

identifying ventricular sensed events occurring within said oversense interval as oversense events when the ventricular sensed events in the oversense interval d not follow a ventricular pace pulse delivered immediately preceding a preceding ventricular sensed event;

counting said oversense events to produce an oversense event count;

comparing the oversense event count with said oversense event criteria; and recording a ventricular EGM epoch in said device memory in response to said oversense event count meeting said oversense event criteria.

24. The method of claim 23 further comprising the step of recording the date and time that the EGM epoch is recorded in device memory, in conjunction with the recording step.

25. The method of claim 23 further comprising the steps of:

timing the actual interval of an oversense event from a preceding pace pulse or ventricular sensed event; and in conjunction with the recording step, recording the timed actual interval with the EGM epoch that is recorded in device memory in association with the oversense event.

26. In an implantable pulse generator having sensing ventricular events through a sensing lead coupled with the ventricle of a patient's heart, a device memory, means for recording a ventricular electrogram (EGM) in said device memory, and means for generating ventricular pace pulses for pacing the heart, a system for recording an EGM epoch in an oversensing condition of ventricular sensed events for a determination of potential sensing lead integrity failure or electromagnetic interference comprising:

means for establishing an oversense interval following a preceding ventricular event or ventricular pace pulse in which a further ventricular sensed event may occur;

means for identifying ventricular sensed events occurring within said oversense interval as oversense events when the ventricular sensed events in the oversense interval do not follow a ventricular pace pulse delivered immediately preceding a preceding ventricular sensed event;

means for counting said oversense events to produce an oversense event count;

means for comparing the oversense event count with said oversense event criteria; and means for recording a ventricular EGM epoch in said device memory in response to a said oversense event count meeting said oversense event criteria.

27. The system of claim 26 further comprising:

means for recording the date and time that the EGM epoch is recorded in said device memory in association with the recorded EGM epoch.

28. The system of claim 26 further comprising:

means for timing the actual interval of an oversense event from a preceding paced or sensed event; and means for recording the timed actual interval with the EGM epoch that is recorded in said device memory in association with the oversense event.

29. In an implantable cardiac medical device having means for providing a cardiac therapy in response to a sensed condition and having a device memory for storage of the cardiac electrogram (EGM), a system for responding to an oversense condition that may incorrectly result in the provision of the therapy comprising:

a ventricular sensing lead having at least one sense electrode positioned in relation to a ventricle of a patient's heart;

ventricular sense amplifier means for sensing electrical signals conducted on the sensing lead including ventricular depolarizations of the patient's heart and providing a ventricular sensed event signal in response thereto;

means for establishing an oversense interval following a ventricular sensed event signal or a ventricular pace pulse;

means for identifying ventricular sensed event signals occurring within said oversense short interval as oversense events;

means for counting said oversense events to produce an oversense event count;

means for comparing the oversense event count with oversense event count criteria; and means for recording a ventricular EGM epoch in said device memory in response to said oversense count meeting said oversense event count criteria.

30. The system of claim 29 further comprising:

means for recording the date and time that the EGM epoch is recorded in said device memory in association with the recorded EGM epoch.

31. The system of claim 29 further comprising:

means for timing the actual interval of an oversense event from a preceding paced or sensed event; and means for recording the timed actual interval with the EGM epoch that is recorded in said device memory in association with the oversense event.

* * * * *